(12) United States Patent
Orth et al.

(10) Patent No.: US 12,070,541 B2
(45) Date of Patent: Aug. 27, 2024

(54) BLOOD PROCESSING APPARATUS AND METHOD FOR DESTROYING CANCER METASTASIS IN VIVO

(71) Applicant: Orth Consulting, LLC, Maineville, OH (US)

(72) Inventors: Donald S. Orth, Cincinnati, OH (US); Roger W. Orth, Cincinnati, OH (US)

(73) Assignee: Orth Consulting, LLC, Maineville, OH (US)

( * ) Notice: Subject to any disclaimer, the term of this patent is extended or adjusted under 35 U.S.C. 154(b) by 0 days.

(21) Appl. No.: 18/323,077

(22) Filed: May 24, 2023

(65) Prior Publication Data
US 2023/0381392 A1 Nov. 30, 2023

Related U.S. Application Data

(60) Provisional application No. 63/345,792, filed on May 25, 2022.

(51) Int. Cl.
*A61M 1/34* (2006.01)
*A61F 2/01* (2006.01)
(Continued)

(52) U.S. Cl.
CPC ............ *A61M 1/3489* (2014.02); *A61F 2/01* (2013.01); *A61F 2/95* (2013.01); *A61K 8/66* (2013.01); *A61M 1/15632* (2022.05); *A61M 1/1621* (2014.02); *A61M 1/1678* (2013.01); *A61M 1/267* (2014.02); *A61M 1/36* (2013.01); *A61M 1/3601* (2014.02); *A61M 1/3618* (2014.02);
(Continued)

(58) Field of Classification Search
CPC ............ A61M 1/15632; A61M 1/1621; A61M 1/1678; A61M 1/267; A61M 1/3489; A61M 1/36; A61M 1/3601; A61M 1/3618; A61M 1/3621; A61M 1/3679; A61M 1/3687; A61M 1/3689; A61M 2202/0445; A61M 2205/3303; A61M 2205/3368; B01D 63/02; B01D 63/06; B01D 69/04; B01D 69/043; B01D 69/08; B01J 31/00; B01J 31/003; C07K 16/00; C07K 16/38; C07K 16/40; C12N 9/22; C12N 11/00; C12N 11/04; C12N 11/06; C12N 11/14; C12N 11/16; A61F 2/01; A61F 2/95; A61K 8/66
See application file for complete search history.

(56) References Cited

U.S. PATENT DOCUMENTS 11,389,581 B1 * 7/2022 Orth ................ B01D 63/02

* cited by examiner

*Primary Examiner* — John Kim
(74) *Attorney, Agent, or Firm* — David R. Stevens; Stevens Law Group

(57) ABSTRACT

A blood treatment method includes the steps of inducing flow of a patient's blood through a blood treatment device inlet and outlet in fluid connection to the circulatory system of the patient. Metastatic deoxyribonucleic acid (DNA) contained within patient blood is destroyed by passing a patient's blood over a bioreactor surface having attached or immobilized deoxyribonuclease 1 (DNase 1) enzyme. The blood treatment device which consists of a bioreactor containing immobilized DNase 1, enables continuous treatment of a patient's blood and increases the effective concentration of DNase 1 in a patient's bloodstream to convert metastasizing cancer DNA in blood into non-oncogenic nucleotide fragments in vivo without adding any chemicals to the blood of the patient.

23 Claims, 5 Drawing Sheets

(51) Int. Cl.
  *A61F 2/95* (2013.01)
  *A61K 8/66* (2006.01)
  *A61M 1/14* (2006.01)
  *A61M 1/16* (2006.01)
  *A61M 1/26* (2006.01)
  *A61M 1/36* (2006.01)
  *B01D 63/02* (2006.01)
  *B01D 63/06* (2006.01)
  *B01D 69/04* (2006.01)
  *B01D 69/08* (2006.01)
  *B01J 31/00* (2006.01)
  *C07K 16/00* (2006.01)
  *C07K 16/38* (2006.01)
  *C07K 16/40* (2006.01)
  *C12N 9/22* (2006.01)
  *C12N 11/00* (2006.01)
  *C12N 11/04* (2006.01)
  *C12N 11/06* (2006.01)
  *C12N 11/14* (2006.01)
  *C12N 11/16* (2006.01)

(52) U.S. Cl.
  CPC ........ *A61M 1/3621* (2013.01); *A61M 1/3679* (2013.01); *A61M 1/3687* (2013.01); *A61M 1/3689* (2014.02); *B01D 63/02* (2013.01); *B01D 63/06* (2013.01); *B01D 69/04* (2013.01); *B01D 69/043* (2013.01); *B01D 69/08* (2013.01); *B01J 31/00* (2013.01); *B01J 31/003* (2013.01); *C07K 16/00* (2013.01); *C07K 16/38* (2013.01); *C07K 16/40* (2013.01); *C12N 9/22* (2013.01); *C12N 11/00* (2013.01); *C12N 11/04* (2013.01); *C12N 11/06* (2013.01); *C12N 11/14* (2013.01); *C12N 11/16* (2013.01); *A61M 2202/0445* (2013.01); *A61M 2205/3303* (2013.01); *A61M 2205/3368* (2013.01)

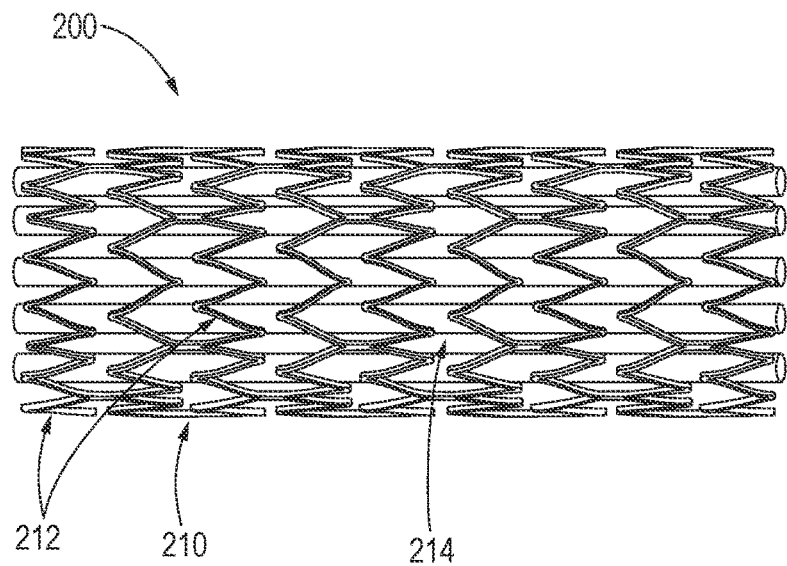
FIG. 2a
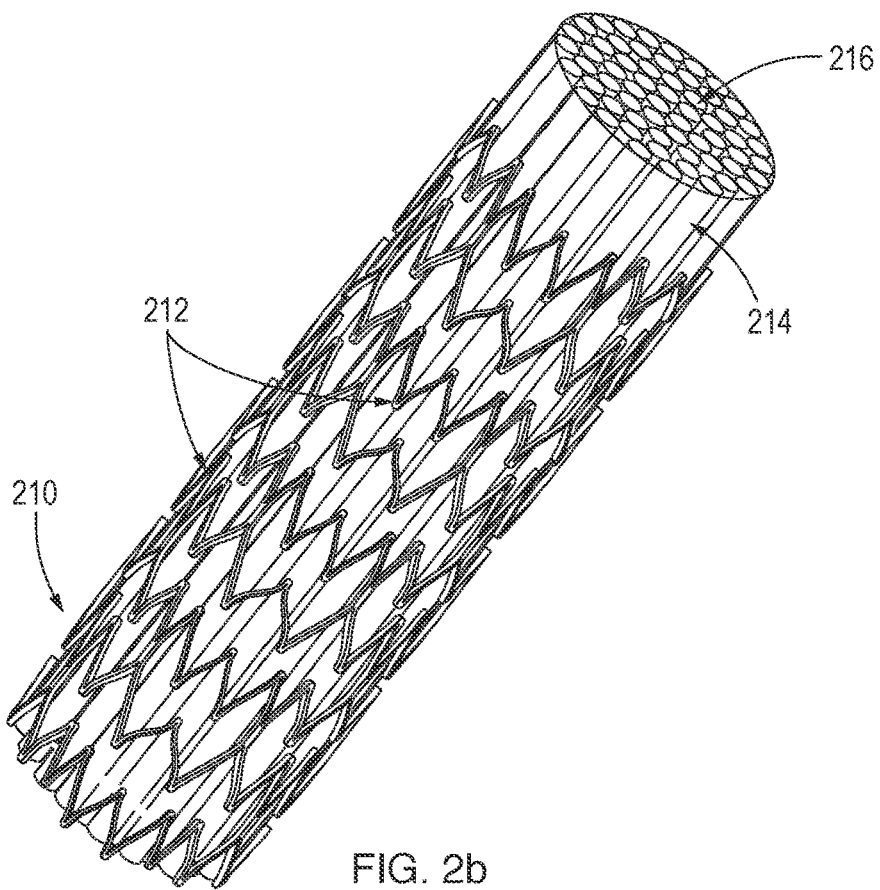
FIG. 2b
FIG. 2

BLOOD PROCESSING APPARATUS AND METHOD FOR DESTROYING CANCER METASTASIS IN VIVO

CROSS-REFERENCE TO RELATED APPLICATIONS

This application claims the benefit of U.S. Provisional Patent Application Ser. No. 63/345,792, filed May 25, 2022, which is hereby incorporated herein by reference in its entirety.

FIELD OF THE INVENTION

This invention relates to prevention of the spread of cancer in a patient by destroying metastatic deoxyribonucleic acid (DNA) in the blood of the patient as this blood passes through bioreactors containing immobilized deoxyribonuclease 1 (DNase 1), an endonuclease that breaks cancer DNA into non-oncogenic fragments. More particularly, a method with blood treatment devices containing immobilized DNase 1 that enables continuous treatment of a patient's blood and increases the effective concentration of DNase 1 in a patient's bloodstream to convert metastasizing cancer DNA in blood into non-oncogenic nucleotide fragments in vivo without adding any chemicals to the blood of the patient, is described.

BACKGROUND OF THE INVENTION

Metastasis is the process by which cancer spreads to different sites in the body, and the majority of deaths due to cancer are due to metastasis of the original tumor cells to organs distant from the original or primary tumor rather than a consequence of the primary tumor. Oncogenes may be present in cells or in cell-free, circulating DNA (cirDNA) that has been released from the primary tumor into the bloodstream.

There is a basal amount of non-metastatic cirDNA in the blood of healthy individuals, and cirDNA may include both nuclear and/or mitochondrial DNA. Although normal, non-tumor cells release DNA into the circulation, it has been demonstrated that the amount of cirDNA in the bloodstream increases with increases in tumor cell number, and more elevated levels of cirDNA are found in the blood from advanced and metastatic cancer patients than in early stage cancer patients. These elevated levels are due to release of DNA from cancer cells because the basal cirDNA levels from normal cells remain constant. In addition, cell-free ribonucleic acid (RNA) can be found in the plasma of cancer patients in various types of cancer including malignant melanoma, breast cancer, colorectal cancer and gastric cancer.

Tumor-associated cirDNAs can play important roles in the promotion of metastasis and DNase 1 can decrease the metastatic spread of tumor cells and inhibit metastases in experimental tumor models. Intramuscular (IM) administration of RNase A (0.35-7 µg/kg) or DNase 1 (0.02-2.3 mg/kg) may result in a considerable decrease in the metastases in murine models. Studies show that cancer causes increases of cirDNA and RNA in the bloodstream and that administration of DNase 1 and RNase A decreases metastases in test animals.

The cirDNA level in plasma of patients with stomach and colon cancer has been found to be increased and the DNase levels were below the detection limits of an associated assay. It has been demonstrated that low DNase activity in blood plasma of cancer patients can cause an increase in the concentration of cirDNA. DNase activity in the blood depends on the concentration of DNase and the presence of inhibitors, such as actin, which forms an inactive 1:1 stoichiometric complex with DNase.

Neutrophils form neutrophil extracellular traps (NETs), which are meshes of DNA with cytotoxic enzymes that are released extracellularly to trap and kill infecting microorganisms. NETs induced within the vasculature by experimentally induced bacterial infection or surgical stress were found to aid metastatic spreading of cancer cells in the livers of mice. It has been proposed that the modest effects of DNase 1 in preventing metastases in vivo in associated studies were due to the short half-life of DNase 1 in blood because higher concentrations of DNase 1 were found in plasma when mice were injected with DNase 1-coated nanoparticles than when injected with free DNase 1. One study observed that DNase may completely dissolve NETs in vitro. Another study reported that surgical stress resulted in formation of NETs that promoted the development and progression of liver metastases. The study reported that surgical stress was associated with a substantial increase in hepatic metastatic disease and that both DNase and inhibition of peptidyl arginine deiminase type IV (PAD4), an enzyme required for NET formation, reduced metastases due to reduced formation of NETs, which produced favorable oncologic outcomes in mice. PAD4 is expressed in neutrophils and drives the formation of NETs when neutrophils are activated. The peptidyl arginine deiminase family of enzymes, including PAD4, is responsible for citrullination of nuclear histones, the irreversible conversion of arginine into citrulline, which leads to decondensation of chromatin. This is a key step in formation of NETs and release of histones which contribute to endothelial damage and organ failure in sepsis. Contemporary reports highlight the value of PAD4 inhibitors to prevent the formation of NETs and use of DNase to destroy NET-DNA to help prevent cancer metastases after surgery.

Manipulation of primary tumors during surgery may be associated with increased numbers of circulating tumor cells, and tumor cell entrapment within NETs promoted stable retention that permitted tumor invasion and growth in the liver and lungs of experimental animals. It has been demonstrated that cancer cells can become trapped within NETs in vitro, and that invasion of liver cells in vitro was abrogated by the addition of 1,000 U DNase 1 or 5 M neutrophil elastase inhibitor (NEi). One study reported that NET-DNA acted as a chemotactic factor to attract cancer cells, rather than merely trapping metastatic cancer cells in mouse models. Other studies have reported that the basal concentration of DNA in the blood of cancer patients was higher than in healthy individuals.

Indwelling vascular devices include arterial and intravenous (IV) stents and catheters that are used to maintain patency, access blood, and administer IV fluids and medications to a patient. First generation stents, such as bare metal stents (BMS) made from 316L stainless steel, have been successful in maintaining blood flow in patients with atherosclerosis or blocked arteries. Drug eluting stents (DES) are made of a polymer that protects the medicine and releases it in a controlled manner over a period of time. Research has reported that polyethylene II vascular catheters were safe and provided long-indwelling vascular access for weeks, months or years in patients with cancer.

Indwelling catheters for use in blood vessels generally are thin, flexible tubes, and stents are expandable metal or polymer devices that are inserted into a blood vessel, typically an artery, and expanded to maintain patency of that vessel. It is possible to enhance catheters and stents for immobilization of enzymes and proteins by incorporating hollow fiber bundles into catheters and stents to increase the interior surface area for immobilized enzymes and other materials. The fiber bundles in such devices may be made from biocompatible materials including polyamide (nylon), polysulfone, polyether sulfone, polyvinylidene fluoride, and cellulose di- and tri-acetate. The fibers in the hollow-fiber bundles should have inner diameters of 50-500 µm to provide substantial surface area for immobilizing bioactive materials including enzymes and enzyme inhibitors and have sufficient diameter so to allow red blood cells, platelets, granulocytes, macrophages and neutrophils to pass through the fibers without restricting blood flow.

Immunotherapy using monoclonal antibodies (mAbs) is a type of targeted cancer therapy that uses mAbs to block specific targets on cancer cells or flag the cancer cells for destruction by the immune system. mAbs bind to target ligands and are thereby unavailable for further treatment so that repeated IV injections of the mAbs may be needed to maintain the desired concentration of such mAbs in the bloodstream of the patient. Use of immobilized mAbs would greatly reduce or eliminate the need for repeated injections into a patient; however, the activity of the immobilized mAbs would decrease over time as the binding sites become occupied with target ligands.

Increased intestinal permeability may play a role in some chronic diseases and inflammatory conditions and has been reported for some types of cancer. Increased intestinal permeability allows digestive enzymes including trypsin, chymotrypsin and elastase to escape from the intestinal lumen and move into the wall of the intestine where these enzymes may activate matrix metalloproteinases (MMPs). This increases the overall proteolytic activity which facilitates translocation of Gram negative bacterial lipopolysaccharide (LPS) and these proteases into the bloodstream. Significantly increased levels of trypsin-, chymotrypsin-, and elastase-like enzymes, and MMP-9 in plasma following hemorrhagic shock in rats have been reported. It is likely that similar translocation of proteases would occur during some types of cancer in humans and that such proteases in the bloodstream would cause fibrin formation and conversion of plasminogen into plasmin, which would exacerbate inflammation and tissue damage in cancer. Protease action would also digest enzymes and protein enzyme inhibitors immobilized in blood treatment devices. This could be prevented by use of antibodies against these enzymes and by use of protease inhibitors.

In the human body, the fibrinolytic system functions to dissolve fibrin, one of the main products of thrombin activity. Two serine proteases: tissue plasminogen activator (tPA) and urokinase plasminogen activator (uPA) catalyze the conversion of plasminogen into the broad-spectrum protease plasmin, the major protease in this system. tPA and uPA may be inhibited by serine protease inhibitors (serpins) including plasminogen activator inhibitor-1 (PAI-1) and to a lesser extent, plasminogen activator inhibitor-2 (PAI-2). The fibrinolytic system may be down-regulated by use of antibodies against tPA, uPA, or plasmin and by protease inhibitors.

Complement is part of the innate immune system that protects humans against pathogens; however, it is often identified as an inducer of excessive inflammatory host responses that are believed to contribute to multiple organ failure and death in severe sepsis. The classical complement pathway may be activated by binding of antigen-antibody complexes to one of the C1 proteins, and this is followed by a cascade of reactions. Cleavage of complement C3 by serine proteases including C3 convertase, thrombin, or plasmin leads to formation of C3a and C3b fragments. The anaphylatoxin C3a may activate platelets and cause their aggregation, increase vascular permeability, and promote extravasation of phagocytes. The C3b fragment may participate in opsonization, which involves phagocytosis of antibodies or bacteria, release of inflammatory peptides, and activation of the complement membrane attack complex to cause cell lysis. Protease inhibitors that bind C3 convertase and plasmin would abrogate this process, thereby reducing inflammation and formation of the membrane attack complex that could destabilize enzymes and protein enzyme inhibitors immobilized in the blood treatment devices described herein.

Neutrophils are important in host defense against infections and act as the first line of microorganism control. Neutrophil elastase (NE) is a serine protease that has antibacterial activity against Gram negative bacteria like *Escherichia coli*, it is active against a broad range of substrates, and it is an important factor promoting inflammation. Proteolytic enzymes in blood including elastase, plasmin, thrombin, and the membrane attack complex of complement may promote inflammation and destroy tissues in sepsis. These proteases may also destroy enzymes and protein enzyme inhibitors immobilized in blood treatment devices. This could be prevented by use of antibodies against these enzymes and by use of protease inhibitors.

It is necessary to maintain the activity and stability of enzymes and functional proteins immobilized on indwelling and extracorporeal bioreactors. Use of immobilized proteins that would not be recognized as "foreign" by the patient's immune system would be of paramount importance for preserving enzyme activity and maintaining stability of immobilized enzymes and enzyme inhibitors. This may require use of enzymes and antibodies against specific enzymes and enzyme inhibitors from human blood or tissues or prepared from the patient's blood or tissues by recombinant deoxyribonucleic acid (DNA) technology including antibodies against these proteases (e.g., anti-trypsin, anti-elastase, and anti-MMP-9), serine protein inhibitors (serpins) [e.g., alpha-1 antitrypsin inhibitor (A1AT), plasminogen activator inhibitor-1 (PA-1) and plasminogen activator inhibitor-2 (PA-2)], and $\alpha_2$-macroglobulin, which is able to inactivate a wide variety of proteases including plasmin, elastase, and MMPs.

Immobilization of one or more protease inhibitors or antibodies against these proteolytic enzymes in one or more in-dwelling blood treatment devices (e.g., stents, catheters, and stents and catheters with hollow-fiber constructs) and in extracorporeal bioreactors with hollow-fiber constructs would reduce the levels of the circulating proteases in the bloodstream, thereby reducing the protease destruction of the immobilized enzymes and protein enzyme inhibitors in blood treatment devices that are the subject of this invention. Alternately, one or a plurality of the protease inhibitors may be co-immobilized in the same blood treatment device with one or a plurality of the nuclease enzymes in in-dwelling blood treatment devices including stents, catheters, stents and catheters containing hollow-fiber bundles, and in extracorporeal blood treatment devices containing hollow-fiber bundles.

Generally speaking, preventing metastases in high-risk patients is much better than having to treat these patients. Although an extracorporeal device with DNase 1 for preventing cancer metastasis may be suitable for prophylaxis or treatment of cancer patients, mobility constraints and long-term use may make an indwelling medical device more suitable for some patients. Accordingly, there exists a need in the art for indwelling vascular devices and extracorporeal bioreactors with immobilized DNase 1 that may be used as a sole treatment for destroying elevated cirDNA and cancer metastases in the bloodstream of a patient or as adjuncts to other treatments for prevention and treatment of cancer.

BRIEF SUMMARY OF THE INVENTION

This disclosure describes a system, apparatus and method that can accomplish therapeutic destruction of selected nucleic acids within a biological system, including but not limited to those produced by cancer cells in humans and animals, and more specifically, destruction of metastasizing cancer cells, cirDNA and NET-DNA in the blood of a patient to prevent cancer metastasis by continuous passage of the blood of the patient through blood treatment devices consisting of indwelling or extracorporeal bioreactors containing immobilized nuclease enzymes, such as DNase 1.

BRIEF DESCRIPTION OF THE DRAWINGS

Embodiments will be readily understood by the following detailed description in conjunction with the accompanying drawings.

FIG. 2 illustrates one embodiment of an indwelling vascular device comprising a stent with a hollow fiber bundle.

DETAILED DESCRIPTION OF THE INVENTION

Figure 1:
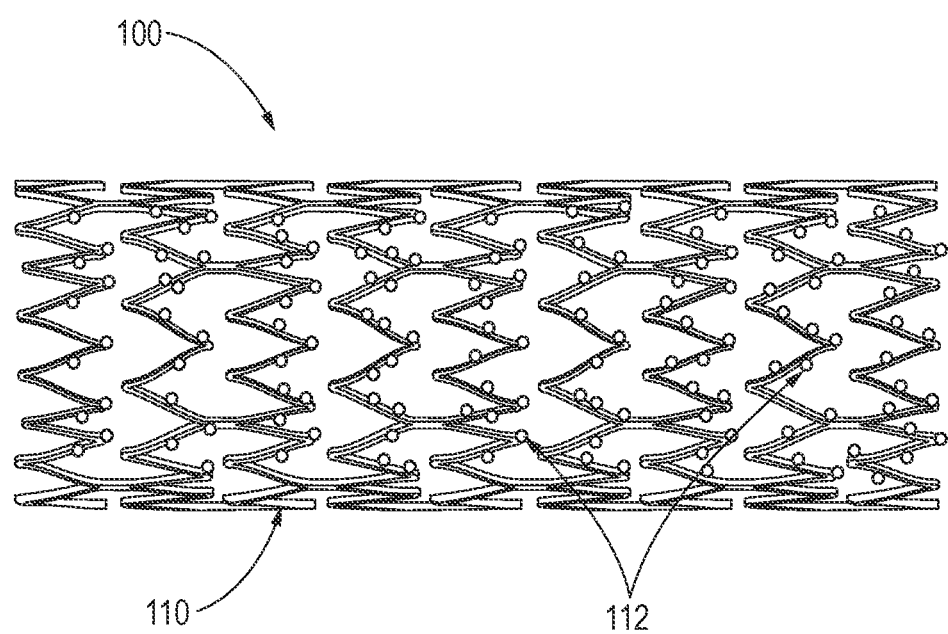
FIG. 1 illustrates one embodiment of an indwelling vascular device comprising a stent with immobilized enzymes, which can be inserted into the circulatory system of a patient to receive and treat blood in a patient to prevent metastasis.

This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, the term "about", when used in reference to numerical ranges, cutoffs, or specific values, is used to indicate that the recited values may vary by up to as much as 10% from the listed value. As many of the numerical values used herein are experimentally determined, it should be understood by those skilled in the art that such determinations can, and often times, will vary among different experiments. The values used herein should not be considered unduly limiting by virtue of this inherent variation. The term "about" is used to encompass variations of this sort up to, or equaling, 10%.

The term "attach," "attached" or "attachment" as used herein, refers to connecting or uniting by a chemical bond, link, or force in order to keep two or more chemical compounds, polymers, proteins, polysaccharides, lipids, nucleic acids, or other biological or manufactured compositions together.

As used herein, "for example," "for instance," "such as," or "including" are meant to introduce examples that further clarify a more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

Disclosed herein are vascular treatment devices, systems or methods involving circulating, perfusing, or otherwise passing blood or other patient fluids through a system and device surgically implanted into or connected to the body. One or more internal surfaces of this system include immobilized enzymatic agents to interact with one or more patient fluid borne biologic agents. The indwelling vascular and extracorporeal devices, systems or methods provide a platform that can be applied to numerous types of cancer to hydrolyze DNA in metastasizing cancer cells, cirDNA, NET-DNA, and cirDNA complexed with serum proteins or cell-free membrane constituents in the blood of a patient to disrupt metastasis and prevent the spread of cancer from the primary tumor to other sites in the body. The foregoing discussion indicates that there are elevated levels of cirDNA and decreased levels of DNase 1 in the blood of cancer patients, so treatment of such patients with DNase 1 increases the effective concentration of DNase 1 in the bloodstream to help prevent cancer metastasis.

One of the problems with IV administration of DNase 1 is its short half-life. Generally, DNase immobilized on nanoparticles degrade DNA for up to 32 h; however, 32 h may be insufficient for preventing cancer metastasis so that repeated injections of this DNase 1 and sampling of the patient's blood, analytical testing to determine the concentration of DNase 1 in this blood, and repeated injections would be needed to maintain DNase 1 levels at the proper therapeutic concentration in the blood of the patient. The DNase immobilized on nanoparticles can accumulate in the liver and kidneys, which suggests that the nanoparticles may not be readily metabolized in the liver or excreted by the kidneys, so use in patients may be contraindicated. The invention described herein uses indwelling vascular devices with DNase 1 immobilized on the blood-contact surfaces and surgically inserted into the circulatory system of a patient or an extracorporeal bioreactor with DNase 1 immobilized on the surfaces of a hollow fiber bundle and connected to the circulatory system of a patient, to increase the effective concentration of DNase 1 in the blood of the patient. This enables continuous treatment of a patient's blood for days, weeks or months without adding chemicals to the blood of the patient—no antibiotics, antibodies, chemotherapeutic agents, hydrolytic enzymes, anti-coagulants such as heparin or sodium citrate, or anti-inflammatory agents are needed. This makes these devices ideally suited for use as a stand-alone treatment or as an adjunct to other treatments of cancer and sepsis.

Surgical procedures, microbial infections including sepsis, and chemotherapy that causes tissue damage may result in the release of cancer cells and cirDNA from tumor cells and recruitment of neutrophils that release NETs to form NET-DNA which may entrap cancer cells, facilitate their metastasis by transmission to distant sites in the body via the bloodstream, and aid invasion of the cancer cells into susceptible host cells. The cirDNA and NET-DNA levels are elevated and the DNase 1 levels in the bloodstream are lower in cancer patients than in people without cancer, so restoration of DNase 1 levels in the bloodstream by treatments that increase the effective concentration of DNase 1 to destroy metastatic cancer cells, cirDNA and NET-DNA is a viable option for preventing cancer metastasis.

The objective of this invention is to prevent the metastasis of cancer in the blood of a human or animal patient by use of vascular and extracorporeal blood treatment devices consisting of nuclease enzymes, such as DNase 1, immobilized in a bioreactor to increase the effective concentration of DNase 1 in the patient's bloodstream and destroy metastatic cells, cirDNA and NET-DNA by hydrolytic cleavage of phosphodiester linkages in the backbone of the cancer DNA as the patient's blood passes through this bioreactor. Such enzymatic action prevents cancer metastasis from a primary tumor to other sites in the patient's body. Treatment of a patient with the blood treatment apparatus and method described herein may be done continuously without addition of any chemicals to the blood of the patient, which eliminates the need for repeated injections/infusion of DNase 1, repetitive sampling of the patient's blood, and testing to determine if levels of the added DNase 1 are within the proper therapeutic range to prevent metastasis of tumor DNA.

In one embodiment, the indwelling vascular device with DNase 1 enzyme immobilized by covalent attachment to the bioreactor surface is integrated or implanted into the circulatory system of a patient to allow treatment of the patient's blood as it passes through the bioreactor inlet and outlet in fluid connection to the circulatory system of the patient.

In one embodiment, the bioreactor surface is provided with a continuous blood flow from the patient to reduce the metastatic cirDNA and NET-DNA being hydrolyzed to undetectable levels.

In one embodiment of this invention, the indwelling vascular device is a stent with immobilized DNase 1 which allows treatment of a patient's blood to destroy cancer cells, metastatic cirDNA and NET-DNA. Although a patient may be treated in this manner with an extracorporeal blood treatment apparatus, there may be medical conditions for which it would be preferable to have continuous, long-term treatment, for example, over a period of weeks or months, so that it would be more suitable to have an indwelling bioreactor rather than to have an extracorporeal bioreactor for treating a patient's blood that may limit a patient's activities because such an extracorporeal device would require a blood transfer line from a blood vessel of the patient to the bioreactor, a blood transfer line from the bioreactor back to a blood vessel of the patient, and a pump for transferring blood from the patient to the bioreactor and back to the patient. A blood treatment device with immobilized DNase 1 may be used as a sole treatment device for preventing cancer metastasis or as an adjunct to other cancer prevention and treatment procedures.

In one embodiment of this invention, the vascular bioreactor is a single indwelling catheter with immobilized DNase 1 which allows treatment of a patient's blood to destroy cancer cells, metastatic cirDNA and NET-DNA.

In one embodiment of this invention, the use of a plurality of indwelling stents comprised of immobilized DNase 1 in the one stent and immobilized biological agents in the other stents that prevent inactivation of the immobilized DNase 1 or improve the efficacy of this immobilized DNase 1, thereby maintaining activity of DNase 1 in the bloodstream of a patient to insure destruction of cancer cells, metastatic cirDNA and NET-DNA in a patient's blood, without adding any chemicals to the blood of the patient.

In one embodiment of this invention, the use of a plurality of indwelling catheters comprised of immobilized DNase 1 in the one catheter and immobilized biological agents in the other catheters that prevent inactivation of the immobilized DNase 1 or improve the efficacy of this immobilized DNase 1, thereby maintaining activity of DNase 1 in the bloodstream of a patient to insure destruction of cancer cells, metastatic cirDNA and NET-DNA in a patient's blood, without adding any chemicals to the blood of the patient.

In one embodiment, a blood treatment method includes the steps of surgical implantation of the stent with immobilized DNase 1 into an artery of a patient. Metastatic cancer cells, cirDNA and NET-DNA contained within the blood of a patient can be rendered non-oncogenic as the patient's blood is passed over a bioreactor surface having attached or immobilized endonuclease enzymes, with the bioreactor being contained within the stent.

In one embodiment, a blood treatment method includes the steps of surgical implantation of the catheter with immobilized DNase 1 in an artery of a patient. Metastatic cancer cells, cirDNA and NET-DNA contained within the blood of a patient can be rendered non-oncogenic as the patient's blood is passed over a bioreactor surface having attached or immobilized endonuclease enzymes, with the bioreactor being contained within the stent.

In one embodiment, the bioreactor may be a stent with a hollow fiber bundle.

In one embodiment, the bioreactor may be a catheter with a hollow fiber bundle.

In one embodiment of this invention, the blood treatment device is an extracorporeal bioreactor with DNase 1 immobilized in a hollow fiber bundle contained therein. This bioreactor allows treatment of a patient's blood to destroy cancer cells, metastatic cirDNA and NET-DNA. It would be necessary to use an extracorporeal bioreactor for treating cancer in situations where immediate treatment is needed or when a patient's physical condition will not allow surgery.

In one embodiment, the endonuclease is DNase 1. The DNase 1 hydrolyzes at least one of metastatic cirDNA, NET-DNA, and cirDNA complexed with serum proteins or cell-free membrane constituents in the blood of a patient, thereby hydrolyzing metastatic DNA to form nucleotide fragments that are not carcinogenic.

In one embodiment, the immobilized DNase 1 in the bioreactor destroys metastatic DNA contained within the blood of a patient by catalyzing the hydrolytic cleavage of phosphodiester linkages in the DNA backbone, thus degrading DNA to form non-oncogenic nucleotide fragments, thereby preventing metastasis from the primary tumor to other sites in the body.

In one embodiment, the immobilized DNase 1 and immobilized monoclonal antibodies against actin (e.g., anti-actin) are used in bioreactors in series so that immobilized monoclonal anti-actin antibodies can bind to actin released from damaged tissues into the bloodstream of the patient, thereby preventing this actin from interfering with immobilized DNase 1 activity as this blood passes through the bioreactor. The first bioreactor with immobilized DNase 1 destroys metastatic cirDNA by catalyzing the hydrolytic cleavage of phosphodiester linkages in the DNA, and the second bioreactor with immobilized anti-actin complexes with actin, thereby reducing the actin concentration in circulating blood of the patient. This enables the DNase 1 in the first bioreactor to remain active for many weeks to destroy metastatic cancer cells, cirDNA and NET-DNA contained within the blood of a patient, thereby preventing metastasis from the primary tumor to other sites in the body.

In one embodiment, the bioreactor surfaces are the inner surfaces of a stent.

In one embodiment, the bioreactor surfaces are the one or more surfaces of a hollow fiber bundle within a stent.

In one embodiment, the bioreactor surface is the inner surface of a catheter.

In one embodiment, the bioreactor surfaces are the one or more surfaces of a hollow fiber bundle within a catheter.

In one embodiment, the bioreactor surfaces are the one or more surfaces of a hollow fiber bundle within an extracorporeal bioreactor.

In one embodiment, the hollow fiber bundle comprises 400 to 20,000 biocompatible hollow fibers made from synthetic materials including, but not limited to polysulfone, polyether sulfone, polymethylmethacrylate, ethylene vinyl alcohol copolymers, polyvinylidene fluoride (PVDF), and polyacrylonitrile, or made from natural materials including, but not limited to cellulose diacetate and cellulose triacetate, with internal diameters of 50-500 µm, a wall thickness of 10 to 100 µm, and a length of 3 to 50 cm. The hollow fibers are arranged in parallel in the hollow fiber bundle, and a dialyzer, such as a kidney dialyzer that contains biocompatible hollow fibers, would be a suitable platform for immobilization of enzymes for the treatment of a patient's blood In one embodiment, DNase 1 enzymes and anti-actin each are immobilized by being covalently attached to separate bioreactor surfaces configured in series.

In one embodiment, DNase 1 enzymes and anti-actin are co-immobilized by being covalently attached to a single bioreactor surface.

In one embodiment, DNase 1 enzymes and anti-trypsin each are immobilized by being covalently attached to separate bioreactor surfaces configured in series.

In one embodiment, DNase 1 enzymes and anti-trypsin are co-immobilized by being covalently attached to the same bioreactor surface.

In one embodiment, DNase 1 enzymes and anti-elastase each are immobilized by being covalently attached to separate bioreactor surfaces configured in series.

In one embodiment, DNase 1 enzymes and anti-elastase are co-immobilized by being covalently attached to the same bioreactor surface.

In one embodiment, DNase 1 enzymes and $\alpha_2$-macroglobulin each are immobilized by being covalently attached to separate bioreactor surfaces configured in series.

In one embodiment, DNase 1 enzymes and $\alpha_2$-macroglobulin are co-immobilized by being covalently attached to the same bioreactor surface.

In one embodiment, DNase 1 enzymes and alpha-1 antitrypsin inhibitor (A1AT) each are immobilized by being covalently attached to separate bioreactor surfaces configured in series.

In one embodiment, DNase 1 enzymes and A1AT are co-immobilized by being covalently attached to the same bioreactor surface.

In one embodiment, DNase 1 enzymes and plasminogen activator inhibitor-1 (PAI-1) each are immobilized by being covalently attached to separate bioreactor surfaces configured in series.

In one embodiment, DNase 1 enzymes and PAI-1 are co-immobilized by being covalently attached to the same bioreactor surface.

In one embodiment, the bioreactor surface further comprises one or more surfaces of a plurality of hollow fiber bundles within a stent.

In one embodiment, the bioreactor surface further comprises one or more surfaces of a plurality of hollow fiber bundles within a catheter.

In one embodiment, the bioreactor surface further comprises one or more surfaces of a hollow fiber bundle within an extracorporeal bioreactor.

In one embodiment, the bioreactor surface further comprises one or more surfaces of one or a plurality of hollow fiber bundles within an extracorporeal bioreactor.

In one embodiment, the hollow fiber bundle for stents comprises 400 to 1,000 polysulfone fibers with internal diameters of 50-500 µm and a length of 3-10 cm. The hollow fiber bundle is enclosed within the stent.

In one embodiment, the hollow fiber bundle for catheters comprises 400 to 1,000 polysulfone fibers with internal diameters of 50-500 µm and a length of 3-10 cm. The hollow fiber bundle is enclosed in biocompatible tubing including, but not limited to Tygon® (silicone) and polyurethane II tubing.

In one embodiment, the hollow fiber bundle for extracorporeal bioreactors comprises 400 to 20,000 polysulfone fibers with internal diameters of 50-500 µm and a length of 3-25 cm enclosed in Tygon® (silicone) or polyurethane II tubing.

In one embodiment, the bioreactor is comprised of a nickel-titanium alloy stent.

In one embodiment, the bioreactor is comprised of a hollow fiber bundle within a nickel-titanium alloy stent.

In one embodiment, the bioreactor is comprised of a 316L stainless steel stent.

In one embodiment, the bioreactor is comprised of a hollow fiber bundle within a 316L stainless steel stent.

In one embodiment, the bioreactor is comprised of a polysulfone hollow fiber bundle within a 316L stainless steel stent.

In one embodiment, the bioreactor is comprised of a cellulose triacetate hollow fiber bundle within a 316L stainless steel stent.

In one embodiment, the bioreactor is comprised of a polyether sulfone hollow fiber bundle within an extracorporeal blood treatment device.

In one embodiment, the bioreactor is comprised of a polysulfone hollow fiber bundle within an extracorporeal blood treatment device.

In one embodiment, the bioreactor is comprised of a polyurethane II catheter.

In one embodiment, the bioreactor is comprised of a hollow fiber bundle within a polyurethane II catheter.

In one embodiment, the bioreactor is comprised of a polysulfone hollow fiber bundle within a polyurethane II catheter.

In one embodiment, nuclease enzymes including DNase 1 are used to destroy metastatic cirDNA in the bloodstream of a patient to therapeutically treat at least one of brain cancer (such as glioblastoma), thyroid cancer, nerve cancer (such as Schwannomas and neurofibrosarcoma), sarcomas that develop from connective tissues including muscle, fat, and blood vessels, breast cancer, lung cancer, bone cancer, liver cancer, esophageal cancer, pancreatic cancer, throat cancer, stomach cancer, intestinal cancer, colorectal cancer, kidney cancer, bladder cancer, prostate cancer, uterine cancer, cervical cancer, testis cancer, ovarian cancer, cardiac cancer, and skin cancers including malignant melanoma, squamous cell carcinoma, and basal cell carcinoma.

The vascular blood treatment apparatus and method described herein are superior to IV therapies for preventing cancer metastasis that involve administration of DNase 1 into the bloodstream of the patient that may require repetitive sampling and testing of the patient's blood along with repeated injections of DNase 1 into the blood to maintain proper therapeutic levels. In addition, immobilized DNase 1 may have a longer half-life in the blood of a patient than IV administration of the same amount of free DNase 1 because immobilized enzymes have greater stability than their free counterparts.

Adverse immunological responses or platelet activation and blood clotting as a result of contact with a 'foreign' enzyme in the bloodstream may be avoided by performing a liquid biopsy on the blood of the patient, harvesting the DNase 1 contained therein, immobilizing this DNase 1 on the surfaces of a stent, such as a BMS, or on the surfaces of a hollow fiber bundle in an extracorporeal reactor, so that the DNase 1 is the patient's DNase 1. If it appears unfeasible to obtain enough of the patient's DNase 1 by use of liquid biopsy, the patient's DNase 1 could be synthesized by use of recombinant DNA technologies and immobilized on a stent, catheter, or extracorporeal bioreactor as described herein.

DETAILED DESCRIPTION OF THE DRAWINGS

FIG. 1 illustrates a BMS 110 with immobilized DNase 1 112 covalently bonded to the surfaces of this BMS 110. This stent may be surgically implanted into the circulatory system of a patient to increase the effective concentration of DNase 1 in the bloodstream of this patient to prevent cancer metastasis.

FIG. 2 illustrates one embodiment of a blood treatment device 200 comprising a stent 210 with stainless steel metal components 212. FIG. 2a shows the stent 210 placed horizontally, and the hollow fiber bundle 214 is surrounded by the stainless steel metal components 212 of the stent 210. FIG. 2b shows the stent 210 positioned at a 45-degree angle from horizontal. The hollow fiber bundle 214 is surrounded by the metal components 212 of the stent 210, and the circular openings 216 of many tubes in the hollow fiber bundle 214 are shown.

Figure 3:
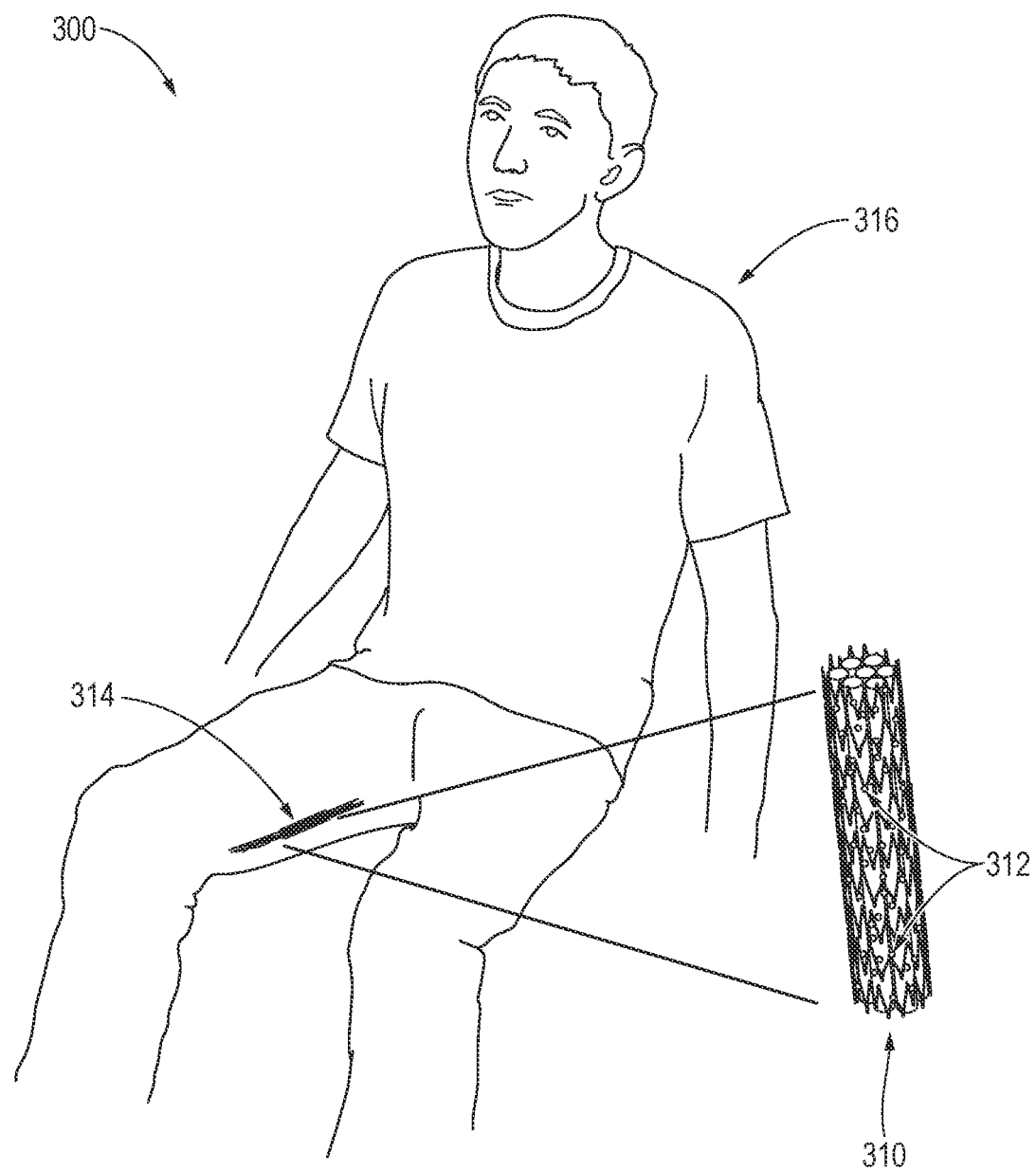
FIG. 3 illustrates one embodiment of an indwelling stent containing a hollow fiber bundle with immobilized enzymes, implanted into the right femoral artery of a patient to receive and treat blood.

FIG. 3 illustrates a system or bioreactor that comprises an indwelling stent 310, onto which is immobilized 1,000 U DNase 1 312. The stent 310 has an inlet 318 and outlet 320 in fluid connection with the bloodstream of the patient. This stent is surgically implanted into the right femoral vein 314 of a patient 316. The patient's heart pumps blood into the inlet 318 of the stent 310, where immobilized DNase 1 312 hydrolyzes cirDNA, NET-DNA, and DNA in metastasizing cancer cells in the blood as the blood passes through the bioreactor, and then the treated blood exits the bioreactor 310 via the outlet 320. In some embodiments, the stent 310 can form the entirety of the medical device. Alternately, the stent 310 can be connected in series with other blood treatment devices containing immobilized agents to help maintain enzymatic activity of the DNase immobilized in the bioreactor. The patient's blood may be sampled periodically so that this blood can be tested to determine the efficacy of metastatic DNA destruction. This process should be continued until the primary tumor is eliminated, which may require surgical removal or killing of the tumor cells by irradiation or chemotherapy, with continued DNase 1 treatment of the patient's blood with the bioreactor 310 to insure complete destruction of metastatic cirDNA in the blood of the patient. Although drugs, chemotherapeutic agents, and fluids may be administered to the patient as part of the treatment of cancer, sepsis, or other medical condition, operation of the implanted stent described herein does not require a pump to urge the blood of a patient through the stent or the addition of any chemicals to the blood of the patient.

In another embodiment of the device, system, or method of FIG. 3, various types of nucleases can be used, including but not limited to human or animal derived endonuclease enzymes including DNase 1, bovine pancreas DNase 1, recombinant human pancreas DNase 1, RNase enzymes including RNase A, and staphylococcal nuclease. Endonuclease enzymes 'break' the cancer-derived DNA and RNA, thereby rendering these oncogenic nucleic acids unable to initiate cancer at another site in the body.

In one embodiment of the device, system, or method of FIG. 3, attachment of enzymatic biologic agents such as DNase 1 can include linkage using conventional affinity tag binding, attachment or adsorption, and enzymatic cross linkage to create an enzymatically reactive surface, or covalent bonding. Covalent bonding can be random or site specific. Amino, thiol, carboxyl, cyanogen bromide, or metaperiodate activation can be used. In some embodiments, discrete linking agents that are attached between the DNase 1 and a surface can be used. In some embodiments, surfaces can be chemically modified to allow enzyme attachment, or functional groups exposed on the surface can be activated. Covalent or ionic coupling a linking agent or enzyme to the surface can include linking of one or more functional groups on the surface or the enzyme.

In one embodiment of the device, system, or method of FIG. 3, biologic agents or compounds that interact with the immobilized enzymatic agents can include blood or fluid conveyed cirDNA. More specifically, in other embodiments, at least one of metastatic cancer cell DNA, cirDNA or cirDNA fragments, NET-DNA, and microbial cirDNA including bacterial cirDNA, yeast cirDNA, fungal cirDNA, and viral cirDNA can be hydrolyzed after interaction with immobilized endonuclease enzymes including DNase 1.

In one embodiment of the device, system, or method of FIG. 3, treatable diseases, conditions, or symptoms of humans or animals can include but are not limited to:
1) Stand-alone treatment or in conjunction with other treatment strategies for brain cancer (such as glioblastoma), thyroid cancer, nerve cancer (such as Schwannomas and neurofibrosarcoma), sarcomas that develop from connective tissues including muscle, fat, and blood vessels, breast cancer, lung cancer, bone cancer, thyroid cancer, liver cancer, esophageal cancer, pancreatic cancer, throat cancer, stomach cancer, intestinal cancer, colorectal cancer, kidney cancer, bladder cancer, prostate cancer, uterine cancer, cervical cancer, testis cancer, ovarian cancer, cardiac cancer, throat cancer, and skin cancers including malignant melanoma, squamous cell carcinoma, and basal cell carcinoma.
2) Prophylactic treatment of the blood of a patient after detection of a solid tumor;
3) Prophylactic treatment of the blood of a patient after detection of abnormally high cirDNA with a concurrent decrease in DNase levels in the blood of a patient that may suggest metastasis of a solid tumor;
4) Palliative treatment of the blood of a patient after detection of metastatic cirDNA from one or more tumors;
5) Treatment of the blood of a cancer patient after surgery (e.g., surgical stress) or beginning chemotherapy which may cause an increase in apoptosis or necrosis of tumor cells with accompanying release of cancer cells and cirDNA into the bloodstream of the patient;
6) Treatment of the blood of a patient to abrogate metastasis due to cancer cells, NET-DNA and cirDNA associated with cell fragments released from living and dying tumor cells;
7) Treatment of the blood of a patient due to bacterial, yeast, fungal, protozoan, or viral infections that result in increased levels of metastatic DNA in the bloodstream of a patient;
8) Treatment of the blood of a patient to reduce levels of nucleotides including extracellular DNA and RNA, in the bloodstream that may be elevated following a course of systemic antibiotic treatment or chemotherapy;
9) Treatment of the blood of a patient to increase the effective concentration of DNase 1 in the bloodstream; and
10) Treatment of the blood of a patient to reduce levels of extracellular DNA in the bloodstream that may be elevated following microbial infections including bacterial infections and COVID-19 infections with sepsis.

Figure 4:
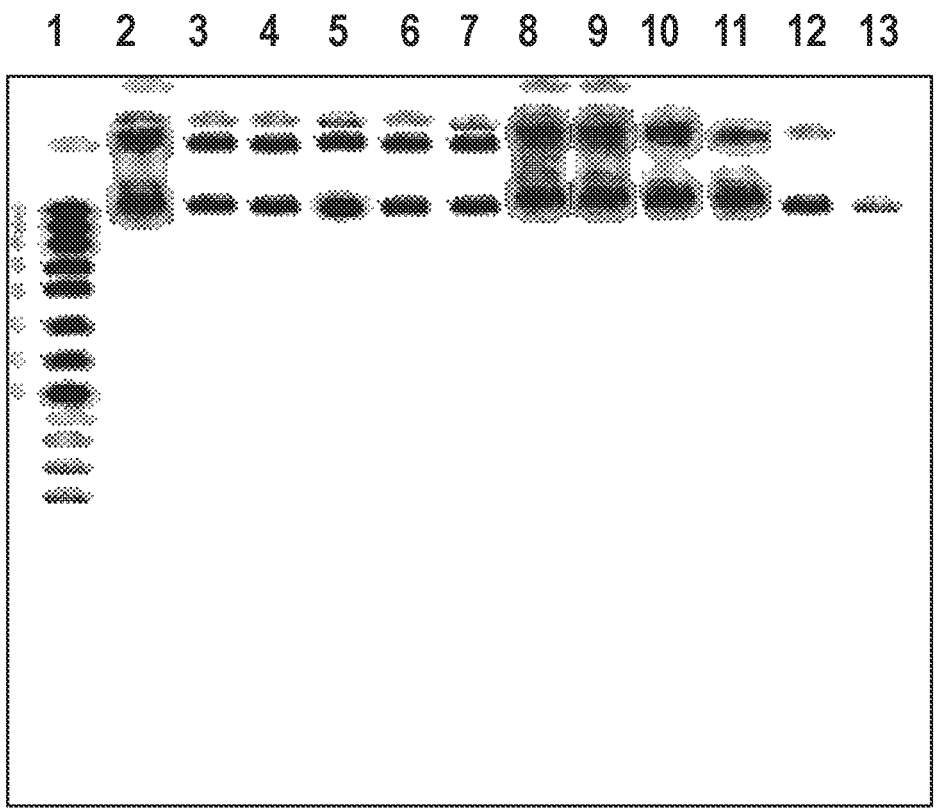
FIG. 4 illustrates an agarose gel following electrophoresis and ethidium bromide staining to reveal destruction of HeLa genomic DNA (gDNA) with DNase 1 immobilized on agarose microbeads in a column after circulation of this gDNA through the column.

FIG. 4 illustrates the results obtained by in vitro use of a bioreactor, a simulated stent consisting of a column containing immobilized DNase 1 on agarose beads (50 µl of 1.6 mg DNase 1 per ml resin). The 125 ng/µl HeLa cell genomic DNA (gDNA) in a buffer system containing 50 mM (N,N-bis(2-hydroxyethyl)-2-aminoethanesulfonic acid (BES), 2 mM CaCl$_2$), and 2.5 mM MgCl$_2$ at pH 7.4 (BES buffer) was passed from the gDNA reservoir, through the column at a flow rate of 0.12 ml/min at room temperature and was recirculated back to the reservoir. Samples were collected from the reservoir initially, and at 30 minute intervals for 150 minutes. The samples at each time point and samples for the controls at each time point were loaded onto 1.5% agarose gel, and electrophoresis was run at 100 V. The destruction of the HeLa cancer cell DNA was determined by fluorescence plate liquid chromatography (FPLC) of samples taken at each time point followed by ethidium bromide staining and densitometry readings by pixel counts of DNA bands in "lanes" in the agarose gel. Pixel readings before the first 30 minutes were not used because the gDNA in the BES buffer was being diluted by the BES buffer in the tubing connected to the column during the first part of the experiment. The destruction of HeLa gDNA by immobilized DNase 1 from 30 to 150 minutes is shown by the decrease in FPLC staining intensity of the DNA bands in the agarose gel lanes 9-13. There was no observable destruction of DNA in the control samples without DNase 1 because no changes in FPLC intensity of the DNA bands were evident in the agarose gel lanes 4-7, which were taken from 30 to 150 minutes.

Figure 5:
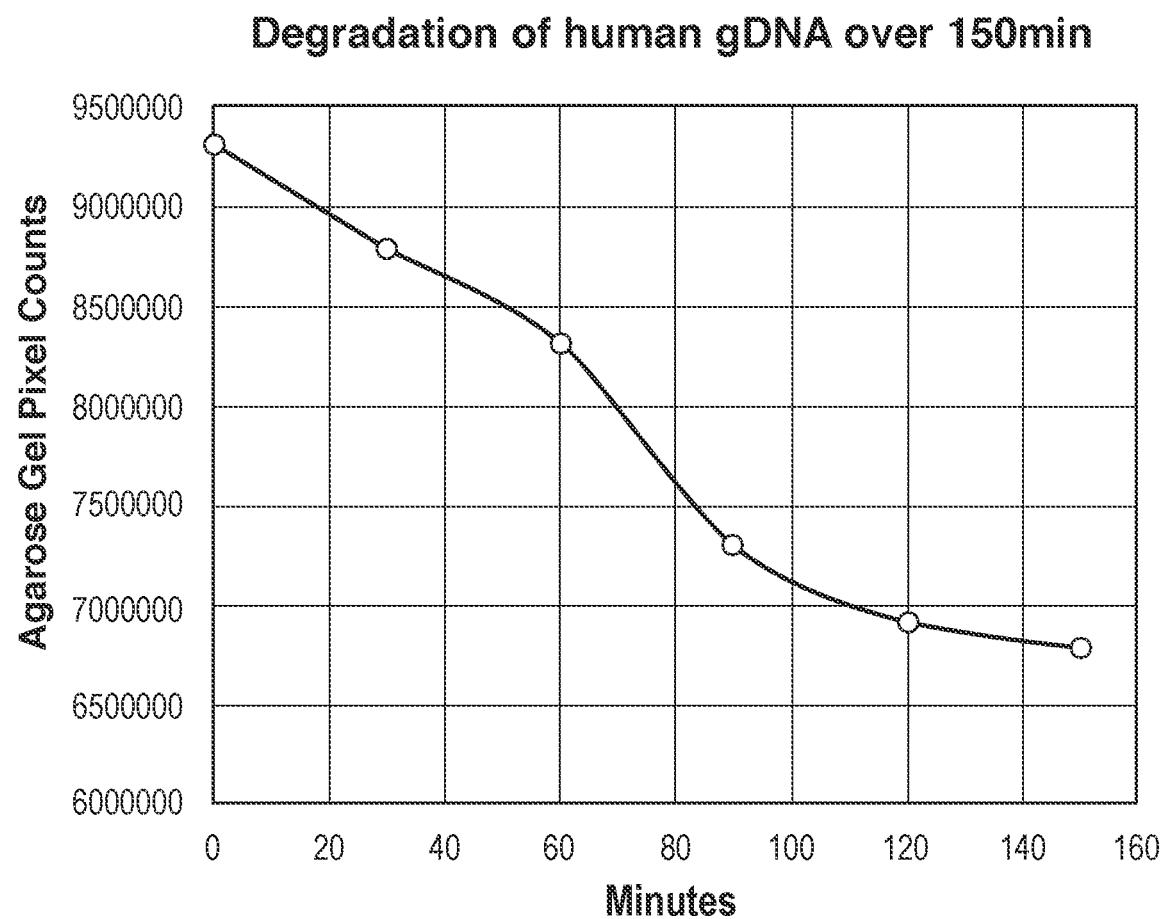
FIG. 5 illustrates the destruction of HeLa cell gDNA in vitro based on image densities of stained HeLa cell gDNA in the agarose gel shown in FIG. 4.

FIG. 5 illustrates the destruction of 125 ng/µl HeLa gDNA in BES buffer circulated through the simulated stent with immobilized DNase 1 using the FPLC image densities of stained HeLa gDNA from 30 to 150 minutes shown in FIG. 4. There was about 23% decrease in stained HeLa gDNA image densities from 30 minutes to 150 minutes, which shows there was a substantial decrease HeLa gDNA concentration in BES buffer during this period. Taken together, FIG. 4 and FIG. 5 show that the simulated stent containing DNase 1 immobilized on agarose microbeads rapidly destroyed HeLa cell cancer DNA in an aqueous buffer at physiological pH (e.g., pH 7.4).

Various modifications to the foregoing described embodiments can be made. For example, a stent or a catheter may be surgically implanted into an artery, into a vein, or between an artery and vein of a patient. In addition, multiple stents or catheters with different biological agents can be implanted in a patient in series to act as bioreactors. Finally, a first stent or catheter may contain immobilized DNase 1 to hydrolyze metastatic cirDNA and a second stent or catheter may contain other immobilized bioactive molecules to help maintain the enzymatic activity of the immobilized DNase 1 in the first stent.

Additional modifications of the foregoing described embodiments include use of an extracorporeal bioreactor connected to a patient with a first blood transfer line that leads to a pump that transfers the patient's blood to the bioreactor comprised of a hollow fiber bundle with immobilized DNase 1, or with immobilized DNase 1 co-immobilized with compounds that protect or maintain the enzymatic activity of DNase 1 in the bioreactor including protease inhibitors and antibodies against proteases, and a second blood transfer line to return treated blood back to the patient.

Example 1

In one example embodiment, a bioreactor comprises a Boston Scientific Innova® self-expanding Nitinol (nickel-titanium) alloy stent, catalog No. 39293-06157, with a length of 150 mm and width of 6 mm, with 2,000 U DNase 1 immobilized on the surfaces of this stent. After immobilization is completed, the stent is placed in a paper or plastic container, which is sealed and sterilized by a dose of 25 kGy ionizing radiation so that it may be used immediately or stored in a refrigerator at 4° C. for several months prior to use. The stent is aseptically removed from the container at the time of surgical implantation.

This sterile Nitinol stent with 2,000 U DNase 1 immobilized on the surfaces may be surgically implanted into the right common femoral vein of a patient shortly after identification of a soft tissue sarcoma of the right gastrocnemius. This stent will prevent metastasis of cancer DNA released into the bloodstream from this sarcoma. The best patient outcome may be obtained by insertion of the Nitrol stent prior to surgical removal of the sarcoma because manipulation of primary tumors during surgery may be associated with increased numbers of circulating tumor cells. The DNase 1 immobilized in the stent destroys approximately 10% of the metastatic cirDNA and NET-DNA in the blood of the patient each hour as the blood passes through this bioreactor, thereby abrogating metastasis of the primary tumor DNA to sites in the body that are distant from the primary tumor. The stability (i.e., half-life) of enzymes generally is increased by immobilization, which enables the stent to retain a substantial percentage of the original immobilized DNase 1 activity while implanted in the patient for up to 6 weeks.

Example 2

In one example embodiment, a bioreactor comprises a titanium oxynitride-coated stainless steel stent, 80 mm long and 5 mm wide, with 1,000 U DNase 1 immobilized on the surfaces of this stent. After immobilization is completed, the stent is placed in a paper or plastic container, which is sealed and sterilized by a dose of 25 kGy ionizing radiation so that it may be used immediately or stored in a refrigerator at 4° C. for several months prior to use. The stent is aseptically removed from the container at the time of surgical implantation.

This sterile titanium oxynitride-coated stainless steel stent with 1,000 U DNase 1 immobilized on the surfaces may be surgically implanted into the left subclavian artery of a patient shortly after identification of breast cancer for prophylactic treatment to prevent metastasis of cancer DNA released into the bloodstream from this cancer, before surgical removal of the breast cancer, and for one month after this surgery. The DNase 1 in the bioreactor destroys approximately 10% of the metastatic cancer cells, cirDNA, NET-DNA, and cirDNA complexed with serum proteins or cell-free membrane constituents in the blood of a patient each hour as the blood passes through this stent, thereby abrogating metastasis of the primary tumor DNA to sites in the body that are distant from this breast cancer. This bioreactor may retain greater than 50% of the original immobilized DNase 1 activity while implanted in the patient for at least one month.

Example 3

In one example embodiment, treatment of a patient is accomplished with two bioreactors in series. The first bioreactor is comprised of a polystyrene stent, 32 mm long and 4 mm wide, in which 100 µg anti-actin monoclonal antibodies are immobilized on the surfaces of the polystyrene stent, and the second bioreactor is comprised of a polystyrene stent, 32 mm long and 4 mm wide, with 1,000 U DNase 1 immobilized on the surfaces of the stent. After the immobilization procedures are completed, the stents are placed in separate paper or plastic containers, which are sealed and sterilized by a dose of 25 kGy ionizing radiation so that these stents may be used immediately or stored in a refrigerator at 4° C. for several months prior to use. The stents are aseptically removed from the containers at the time of surgical implantation.

The sterile polystyrene stents with 1,000 U DNase 1 and 100 µg anti-actin antibodies immobilized on the stent surfaces may be surgically implanted in series into the left femoral artery of a patient shortly after identification of testicular cancer to prevent metastasis of cancer DNA released into the bloodstream from this cancer. The preferred placement of these stents is to have the anti-actin stent being proximal to the groin and the DNase 1 stent placed distal to the groin. The anti-actin antibodies in the bioreactor proximal to the groin bind the actin in the bloodstream of the patient in a 1:1 stochiometric ratio so that this actin cannot complex with and thereby inhibit DNase 1 in the bioreactor distal to the groin. Passage of the blood of the patient through the stent containing DNase 1 destroys approximately 10% of the metastatic cirDNA, NET-DNA, and cirDNA complexed with serum proteins or cell-free membrane constituents in the blood of the patient each hour as the blood passes through this bioreactor, thereby abrogating metastasis of the primary tumor DNA to sites in the body that are distant from the primary testicular cancer. The efficiency of the immobilized anti-actin antibodies decreases with the passage of time because the actin removed from the bloodstream of the patient is bound by the anti-actin antibodies, which prevents these antibodies from binding additional actin in the bloodstream; however, this bioreactor retains a substantial percentage of the original anti-actin antibodies to help preserve the activity of DNase 1 immobilized in the stent that is implanted in the patient for at least 2 months.

Example 4

In one example embodiment, a bioreactor comprises a polyurethane II catheter, 32 mm long and 4 mm wide, with a combination of 50 µM anti-actin monoclonal antibodies and 2,000 U DNase 1 co-immobilized on the inner surfaces of the catheter. After the immobilization procedures are completed, the catheter is placed in a paper or plastic container, which is sealed and sterilized by a dose of 25 kGy ionizing radiation so that the catheter may be used immediately or stored in a refrigerator at 4° C. for several months prior to use. The catheter is aseptically removed from the container at the time of surgical implantation.

This sterile polyurethane II catheter with a combination of 50 µM anti-actin monoclonal antibodies and 2,000 U DNase 1 co-immobilized on the surfaces may be surgically implanted into a distal portion of the patient's left femoral artery and connected to the nearby left femoral vein shortly after identification of kidney cancer to prevent metastasis of cancer DNA released into the bloodstream from this cancer. The anti-actin antibodies in the bioreactor bind the actin in the bloodstream of the patient in a 1:1 stochiometric ratio so that this actin cannot complex with DNase 1 to prevent enzymatic activity, thereby maintaining enzymatic activity of the immobilized DNase 1 in the bioreactor. The immobilized DNase 1 in this bioreactor destroys approximately 10% of the metastatic cirDNA and NET-DNA in the blood of the patient each hour as the blood passes through this bioreactor, which abrogates metastasis of the kidney cancer DNA to sites in the body that are distant from this primary tumor. Polyurethane II catheters may remain in the patient for months or years. This Polyurethane II bioreactor with co-immobilized DNase 1 and anti-actin antibodies retains a substantial percentage of the original immobilized DNase 1 activity while implanted in the patient for at least 3 months.

Example 5

In one example embodiment, treatment of a patient is accomplished with two bioreactors in series. The first bioreactor is comprised of a polystyrene stent, 32 mm long and 4 mm wide, in which 10 mg alpha-1 antitrypsin inhibitor (A1AT) are immobilized on the lumen surfaces of the polystyrene stent, and the second bioreactor is comprised of a polystyrene stent, 32 mm long and 4 mm wide, with 1,000 U DNase 1 immobilized on the lumen surfaces of this stent. After the immobilization procedures are completed, the stents are placed in separate paper or plastic containers, which are sealed and sterilized by a dose of 25 kGy ionizing radiation so that these stents may be used immediately or stored in a refrigerator at 4° C. for several months prior to use. The stents are aseptically removed from the containers at the time of surgical implantation.

The sterile polystyrene stents with 10 mg A1AT immobilized on the lumen surfaces of the first stent and 1,000 U DNase 1 immobilized on the lumen surfaces of the second stent may be surgically implanted in series into the left femoral artery of a patient shortly after identification of lung cancer, to prevent metastasis of cancer DNA released into the bloodstream from this cancer. The preferred placement of the stent containing immobilized A1AT is proximal to the groin, with the stent containing immobilized DNase 1 being distal to the groin. The A1AT in the first bioreactor binds serine proteases in the bloodstream of the patient in a 1:1 stochiometric ratio, thereby preventing proteolytic destruction of the immobilized DNase 1 in the bioreactor. Passage of the blood of the patient through the stent containing DNase 1 destroys approximately 10% of the metastatic cirDNA, NET-DNA, and cirDNA complexed with serum proteins or cell-free membrane constituents in the blood of the patient each hour as the blood passes through this bioreactor, thereby preventing metastasis of the primary tumor DNA to sites in the body that are distant from the primary lung cancer. The binding efficiency of the immobilized A1AT in the first stent decreases with the passage of time because the serine proteases in the bloodstream of the patient are bound by the A1AT, which prevents the A1AT from binding additional proteases in the bloodstream. The second bioreactor retains a substantial percentage of the original immobilized DNase 1 activity while implanted in the patient for 2 months.

Example 6

In one example embodiment, treatment of a patient is accomplished with two bioreactors in series. The first bioreactor is comprised of a polystyrene stent, 32 mm long and 4 mm wide, in which 100 µg neutrophil elastase inhibitor (NEi) are immobilized on the surfaces of the polystyrene stent, and the second bioreactor is comprised of a polystyrene stent, 32 mm long and 4 mm wide, with 1,000 U DNase 1 immobilized on the surfaces of the stent. After the immobilization procedures are completed, the stents are placed in separate paper or plastic containers, which are sealed and sterilized by a dose of 25 kGy ionizing radiation so that these stents may be used immediately or stored in a refrigerator at 4° C. for several months prior to use. The stents are aseptically removed from the containers at the time of surgical implantation.

The sterile polystyrene stents with 100 µg NEi immobilized on the lumen surfaces of the first stent and 1,000 U DNase 1 immobilized on the lumen surfaces of the second stent may be surgically implanted in series into the left femoral artery of a patient shortly after identification of intestinal cancer, to prevent metastasis of cancer DNA released into the bloodstream from this cancer. The preferred placement is to have the stent containing immobilized NEi being proximal to the groin and the stent containing immobilized DNase 1 being distal to the groin. Passage of the blood of the patient through the stent containing DNase 1 destroys approximately 10% of the metastatic cirDNA, NET-DNA, and cirDNA complexed with serum proteins or cell-free membrane constituents in the blood of the patient each hour as the blood passes through this bioreactor and prevents metastasis of the primary tumor DNA to sites in the body that are distant from the primary intestinal cancer. The NEi in the first bioreactor binds the neutrophil elastase in the bloodstream of the patient in a 1:1 stochiometric ratio so that elastase in the bloodstream cannot destroy the immobilized DNase 1 in the bioreactor; however, the binding efficiency of the immobilized NEi in the first stent decreases with the passage of time as the NEi binding sites become occupied with elastase. The immobilized DNase 1 retains a substantial percentage of the original immobilized DNase 1 activity while implanted in the patient for 2 months.

Example 7

In one example embodiment, treatment of a patient is accomplished with two bioreactors in series. The first bioreactor is comprised of a polystyrene stent, 32 mm long and 4 mm wide, in which 100 µg anti-plasmin monoclonal antibodies are immobilized on the surfaces of the polystyrene stent, and the second bioreactor is comprised of a polystyrene catheter, 32 mm long and 4 mm wide, with 1,000 U DNase 1 immobilized on the surfaces of the catheter. After the immobilization procedures are completed, the stent and catheter are placed in separate paper or plastic containers, which are sealed and sterilized by a dose of 25 kGy ionizing radiation so that these stents may be used immediately or stored in a refrigerator at 4° C. for several months prior to use. The stent and catheter are aseptically removed from the containers at the time of surgical implantation.

The sterile polystyrene stent with 100 µg of immobilized anti-plasmin monoclonal antibodies on the lumen surfaces and the catheter with 1,000 U immobilized DNase 1 on the lumen surfaces may be surgically implanted in series into the left external iliac artery of a patient shortly after identification of kidney cancer, to destroy cancer DNA released into the bloodstream from this cancer. The preferred placement is to have the stent containing immobilized anti-plasmin proximal to the heart and the catheter containing immobilized DNase 1 being distal to the heart. The binding efficiency of the immobilized anti-plasmin antibodies in the stent decreases with the passage of time because the plasmin removed from the bloodstream of the patient is bound by the anti-plasmin antibodies, which prevents these anti-plasmin antibodies from binding additional plasmin in the bloodstream. Passage of the blood of the patient through the catheter containing DNase 1 destroys approximately 10% of the metastatic cirDNA, NET-DNA, and cirDNA complexed with serum proteins or cell-free membrane constituents in the blood of the patient each hour as the blood passes through this catheter, thereby preventing metastasis of the primary tumor DNA to sites in the body that are distant from the primary kidney cancer. The second bioreactor retains a substantial percentage of the original immobilized DNase 1 activity while implanted in the patient for 2 months.

Example 8

In one example embodiment, a bioreactor comprises a titanium oxynitride-coated stainless steel stent, 80 mm long and 15 mm wide, with 2,000 U DNase 1 immobilized on the surfaces of the polysulfone hollow fiber bundle 78 mm long and 14 mm wide in this stent. After immobilization is completed, the stent is placed in a paper or plastic container, which is sealed and sterilized by a dose of 25 kGy ionizing radiation so that it may be used immediately or stored in a refrigerator at 4° C. for several months prior to use. The stent is aseptically removed from the container at the time of surgical implantation.

This sterile titanium oxynitride-coated stainless steel stent with 2,000 U DNase 1 immobilized on the inner surfaces of the polysulfone hollow fibers may be surgically implanted into the right subclavian artery of a patient with lung cancer and a COVID-19 infection with sepsis for treatment to destroy cirDNA released from the primary tumor in the lungs. The DNase 1 in the bioreactor destroys approximately 10% of the metastatic DNA in cancer cells, cirDNA and cirDNA complexed with serum proteins or cell-free membrane constituents in the blood of the patient each hour as this blood passes through this bioreactor, thereby preventing cancer metastasis. This bioreactor may retain greater than 50% of the original immobilized DNase 1 activity while implanted in the patient for 2 months.

Example 9

In one example embodiment, a bioreactor comprises an extracorporeal bioreactor comprised of a PVDF hollow fiber bundle 70 mm long and 25 mm wide onto which 2,000 U DNase 1, 10 mg A1AT, and 10 µg anti-plasmin are co-immobilized. After immobilization is completed, the extracorporeal bioreactor is inserted into a polyurethane II sheath that is 80 mm long and 26 mm wide. This extracorporeal bioreactor is then placed in a paper or plastic container, which is sealed and sterilized by a dose of 25 kGy ionizing radiation so that it may be used immediately or stored in a refrigerator at 4° C. for several months prior to use. This bioreactor is aseptically removed from the container at the time it is connected to the patient This extracorporeal bioreactor containing 2,000 DNase 1, 10 mg A1AT and 10 µg anti-plasmin co-immobilized onto the PVDF hollow fiber bundle is attached to a vein in left forearm of a patient, with a blood transfer line running to a peristaltic pump which transfers blood to the extracorporeal PVDF bioreactor, and then returns the treated blood to the same vein via a blood transfer line. The immobilized A1AT and anti-plasmin in the bioreactor bind proteases to help protect the immobilized DNase 1 from proteolytic destruction. The binding ability of A1AT and anti-plasmin decreases over time, but the immobilized DNase 1 maintains a substantial percentage of the original activity while treating the patient for 2 months.

Example 10

In one example embodiment, an extracorporeal bioreactor comprised of a 80 mm long and 26 mm wide polyurethane II tube containing a polyether sulfone hollow fiber bundle 70 mm long and 25 mm wide, onto which 1,000 U recombinant human DNase 1, 1,000 U recombinant human RNase A, and 10 mg recombinant human $\alpha_2$-macroglobulin are co-immobilized. After immobilization is completed, the extracorporeal bioreactor is placed in a paper or plastic container, which is sealed and sterilized by a dose of 25 kGy ionizing radiation so that it may be used immediately or stored in a refrigerator at 4° C. for several months prior to use. This bioreactor is aseptically removed from the container at the time it is connected to the patient.

This extracorporeal bioreactor containing 1,000 DNase 1, 1,000 U RNase A and 10 mg $\alpha_2$-macroglobulin co-immobilized onto the polyether sulfone hollow fiber bundle is attached to a vein in left forearm of a patient, with a blood transfer line running to a peristaltic pump that transfers the patient's blood to the bioreactor, through the bioreactor, and then returns the treated blood to the same vein of the patient via a blood transfer line. The immobilized $\alpha_2$-macroglobulin in the bioreactor binds proteases to help protect the immobilized DNase 1 and RNase A from proteolytic destruction. The binding ability of $\alpha_2$-macroglobulin decreases over time as the binding sites become occupied by proteases, but the immobilized DNase 1 and RNase A maintain substantial percentages of their original activity while treating the patient for 2 months.

Example 11

In one example embodiment, an extracorporeal bioreactor comprised of a 90 mm long and 26 mm wide polyurethane II tube containing a polysulfone hollow fiber bundle, 70 mm long and 25 mm wide, onto which 1,000 U recombinant human DNase 1, 10 mg of monoclonal anti-bodies against peptidyl arginine deiminase type IV (PAD4) (anti-PAD4), and 10 mg recombinant human $\alpha_2$-macroglobulin are co-immobilized. After immobilization is completed, the extracorporeal bioreactor is placed in a paper or plastic container, which is sealed and sterilized by a dose of 25 kGy ionizing radiation so that it may be used immediately or stored in a refrigerator at 4° C. for several months prior to use. This bioreactor is aseptically removed from the container at the time it is connected to the patient.

This extracorporeal bioreactor containing 1,000 DNase 1, 10 mg of anti-PAD4, and 10 mg $\alpha_2$-macroglobulin co-immobilized onto the polysulfone hollow fiber bundle is attached to a vein in left forearm of a patient, with a blood transfer line running to a peristaltic pump which transfers the patient's blood to the bioreactor, through the bioreactor, and then returns the treated blood to the same vein of the patient via a blood transfer line. The immobilized anti-PAD4 binds PAD4 in the bloodstream so that the binding ability decreases over time. Similarly, the binding ability of $\alpha_2$-macroglobulin decreases over time as the binding sites become occupied by proteases in the bloodstream to help protect the immobilized DNase 1 in the bioreactor from proteolytic destruction. The immobilized DNase 1 maintains a substantial percentage of its original activity while treating the patient for 2 months.

Example 12

In one example embodiment, an extracorporeal bioreactor comprised of a 90 mm long and 26 mm wide polyurethane II tube containing a cellulose triacetate hollow fiber bundle, 70 mm long and 25 mm wide, onto which 100 U recombinant human DNase 1, 500 U recombinant human RNase A, 100 µg of monoclonal anti-bodies against peptidyl arginine deiminase type IV (PAD4) (anti-PAD4), and 100 µg recombinant human $\alpha_2$-macroglobulin are co-immobilized. After immobilization is completed, the extracorporeal bioreactor is placed in a paper or plastic container, which is sealed and sterilized by a dose of 25 kGy ionizing radiation so that it may be used immediately or stored in a refrigerator at 4° C. for several months prior to use. This bioreactor is aseptically removed from the container at the time of use.

This extracorporeal bioreactor containing 1,000 U recombinant human DNase 1, 500 mg recombinant human RNase A, 100 µg of anti-PAD4, and 100 µg $\alpha_2$-macroglobulin co-immobilized onto the cellulose triacetate hollow fiber bundle is attached to a blood transfer line from a blood vessel of the patient to a pump for transferring blood from the patient to the bioreactor, to the bioreactor and over the surfaces of the hollow fiber bundle with immobilized DNase 1, RNase A, anti-PAD4, and $\alpha_2$-macroglobulin, and then to a blood transfer line from the bioreactor back to a blood vessel of the patient. The immobilized anti-PAD4 binds PAD4 in the bloodstream so that the binding ability decreases over time. Similarly, the binding ability of $\alpha_2$-macroglobulin decreases over time as the binding sites become occupied by protease ligands in the bloodstream to help protect the immobilized DNase 1 in the bioreactor from proteolytic destruction. The immobilized DNase 1 maintains a substantial percentage of its original activity while treating the patient for 2 months.

Example 13

In one example embodiment, treatment of a patient is accomplished with an extracorporeal bioreactor comprised of a Fresenius Optiflux® F180NR dialyzer containing a polysulfone hollow fiber bundle with a surface area of 1.6 to 2.0 m². 2,000 U human recombinant DNase 1 (hrDNase 1) and 1 mg A1AT are co-immobilized on the Optiflux® hollow fiber bundle of the bioreactor. After the immobilization procedures are completed, the bioreactor is placed in a paper or plastic container, which is sealed and sterilized by a dose of 25 kGy ionizing radiation so that this blood treatment device may be used immediately or stored in a refrigerator at 4° C. for several months prior to use. The blood treatment device is aseptically removed from the container at the time it is connected to the patient.

The sterile Fresenius Optiflux® dialyzer bioreactor with 2,000 U hrDNase 1 and 1 mg of A1AT are co-immobilized on the interior surfaces of the hollow fiber bundle in this bioreactor is connected to a vein in the patient's right forearm, with blood transfer lines leading from the patient to a peristaltic pump, to the Optiflux® bioreactor, and back to a vein in the patient's right forearm shortly after determination that this patient has breast cancer, to prevent metastasis of this cancer. Although the A1AT binding of proteases would help preserve the enzymatic activity of immobilized hrDNase 1, binding to proteases would decrease the efficacy of A1AT binding to other proteases in the bloodstream over time. This bioreactor retains a substantial percentage of the original hrDNase 1 activity for at least 1 month. This example illustrates how enzymes may be immobilized in kidney dialysis assemblies which then can be sterilized and used to treat blood of a patient for cancer and other medical conditions.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

The invention claimed is:

1. A blood treatment method, comprising:
   inducing flow of blood of a human or animal patient through a blood treatment device inlet and outlet to a circulatory system of the patient;
   destroying one or more metastatic agents contained within the blood of the patient by continuously passing the blood of the patient over a bioreactor surface having an attached deoxyribonuclease 1 (DNase 1) enzyme, with the at least one bioreactor surface being contained within the blood treatment device; and
   returning the blood of the patient to the patient for continuous treatment until the metastatic agents have been reduced to predetermined levels, wherein the DNase 1 enzyme comprises human DNase 1 from human blood or tissues or synthetic human DNase 1 from recombinant deoxyribonucleic acid (DNA) technology;
   wherein the DNase 1 enzyme is immobilized and is used prophylactically or therapeutically to increase an effective concentration of DNase 1 in a bloodstream of the patient, and remove one or more nucleic acids within a biological system associated with the patient;
   wherein the nucleic acids include one or more nucleic acids produced by cancer cells in humans and animals;
   wherein the destroying prevents metastasis of tumor cells and metastatic DNA included in the metastatic agents, including circulating DNA (cirDNA) and neutrophil extracellular trap DNA (NET-DNA) in the bloodstream, by passage of the blood of the patient through the blood treatment device and over the bioreactor surface, without adding any chemicals to the blood of the patient;
   wherein the blood treatment device consists of a bioreactor associated with the bioreactor surface; and
   wherein the bioreactor comprises at least one of one or more surfaces of a hollow fiber bundle in a stent.

2. The blood treatment method of claim 1, wherein the hollow fiber bundle comprises 400 to 20,000 biocompatible hollow fibers made from polysulfone, with internal diameters of 50 to 300 µm, a wall thickness of 10 to 100 µm, and a length of 3 to 50 cm, and with the hollow fibers arranged in parallel in the hollow fiber bundle.

3. The blood treatment method of claim 1, wherein the DNase 1 enzyme irreversibly destroys metastatic DNA in the blood of the patient in vivo.

4. The blood treatment method of claim 1, wherein the metastatic DNA includes metastatic nuclear and mitochondrial cirDNA in the blood of the patient.

5. The blood treatment method of claim 1, wherein the DNase 1 enzyme irreversibly detoxifies at least one metastatic agent by hydrolytic cleavage of phosphodiester linkages within one or more polynucleotide chains associated with the metastatic agent, thereby converting the associated metastatic DNA into one or more non-oncogenic nucleotide fragments.

6. The blood treatment method of claim 1, wherein hydrolyzing the metastatic DNA in the blood of the patient is used to therapeutically prevent metastasis of cancer, including at least one of brain cancer, glioblastoma, blood and bone marrow cancers including leukemia, lymphoma and myeloma, thyroid cancer, nerve cancer, Schwannomas, neurofibrosarcoma, sarcomas of connective tissues, sarcomas of nerves, muscles, joints, bone, fat, and blood vessels, breast cancer, lung cancer, bone cancer, liver cancer, esophageal cancer, pancreatic cancer, throat cancer, stomach cancer, intestinal cancer, colorectal cancer, kidney cancer, bladder cancer, prostate cancer, uterine cancer, testis cancer, ovarian cancer, cardiac cancer, throat cancer, and skin cancers including malignant melanoma, squamous cell carcinoma, and basal cell carcinoma.

7. The blood treatment method of claim 1, wherein the DNase 1 enzyme is covalently attached to the bioreactor surface.

8. The blood treatment method of claim 1, wherein the DNase 1 enzyme and a ribonuclease (RNase) A enzyme are covalently attached in series to separate bioreactor surfaces including the bioreactor surface or co-immobilized together on the bioreactor surface.

9. The blood treatment method of claim 1, wherein blood is continuously treated.

10. The blood treatment method of claim 1, wherein blood is circulated through any combination of one or more indwelling stents and catheters associated with the blood treatment device, by blood pressure created by a beating heart of the patient.

11. The blood treatment method of claim 1, further comprising the step of surgical implantation of an indwelling bioreactor into the patient to enable blood of the patient to flow in the following way:
from a first vein through an inlet associated with the indwelling bioreactor and an outlet associated with the bioreactor in fluid connection to the first vein.

12. The blood treatment method of claim 1, further comprising:
surgically implanting a first stent with immobilized DNase 1 into the patient to destroy metastatic DNA in the bloodstream of the patient; and
surgically implanting a second stent with immobilized ribonuclease (RNase) A into the patient to destroy cancer-derived ribonucleic acid (RNA) RNA in the bloodstream, to prevent cancer metastasis.

13. The blood treatment method of claim 1, wherein one or more nuclease enzymes including DNase 1 enzyme and one or more ribonuclease (RNase) A enzymes are covalently attached to the bioreactor surface to destroy the metastatic DNA and metastatic ribonucleic acid (RNA) associated with the metastatic agents in the bloodstream of the patient, to prevent cancer metastasis.

14. The blood treatment method of claim 1, wherein the at least one bioreactor surface is provided with continuous flow of the blood, wherein the flow continues until each metastatic agent being detoxified each has been reduced to a predetermined level.

15. The blood treatment method of claim 1, wherein the DNase 1 enzyme is obtained by harvesting the DNase 1 enzyme from blood or tissues of a cancer patient and immobilizing the DNase 1 enzyme onto the bioreactor surface for treatment of the cancer patient.

16. The blood treatment method of claim 1, wherein one or more nuclease enzymes including DNase 1 enzyme are used prophylactically to treat blood of a patient following surgery, microbial infection, sepsis, and chemotherapy, to prevent cancer metastasis.

17. The blood treatment method of claim 1, wherein the DNase 1 enzyme is used prophylactically to treat the blood of the patient during and following bacterial, yeast, fungal, or viral infections that may result in increased levels of metastatic DNA in the bloodstream of the patient.

18. The blood treatment method of claim 1, wherein the DNase 1 enzyme removes the metastatic DNA from the blood of the patient.

19. The blood treatment method of claim 1, wherein one or more immobilized anti-peptidyl arginine deiminase type IV (PAD4) (anti-PAD4) antibodies are used in combination with one or more nuclease enzymes including the DNase 1 enzyme and one or more ribonuclease (RNase A) A enzymes in the bioreactor to reduce formation of neutrophil extracellular traps (NETs) and release of histones to prevent endothelial cell damage and organ failure in sepsis.

20. The blood treatment method of claim 1, wherein a neutrophil elastase inhibitor (NEi) and the DNase 1 are co-immobilized onto a polysulfones hollow fiber bundle in the bioreactor to reduce neutrophil elastase destruction of tissues in a human or animal patient and elastase destruction of the immobilized DNase 1 in a polysulfones hollow fiber bundle in the bioreactor.

21. The blood treatment method of claim 1, wherein an immobilized anti-protease plasma protein comprising immobilized $\alpha_2$-macroglobulin is used singly or in combination with one or more nuclease enzymes including the DNase 1 enzyme and a ribonuclease (RNase) A enzyme in one or more bioreactors to reduce proteolytic destruction of the immobilized enzymes, anti-protease antibodies, and protease inhibitors, to maintain activity of the immobilized enzymes and proteins in the bioreactor.

22. The blood treatment method of claim 1, wherein one or more antibodies against actin and the DNase 1 are co-immobilized onto a polysulfone hollow fiber bundle in the bioreactor to reduce actin complexation with the immobilized DNase 1 in the bioreactor, thereby maintaining an enzymatic activity of the immobilized DNase 1.

23. The blood treatment method of claim 1, wherein the DNase 1 enzyme and one or more ribonuclease (RNase) A enzymes are immobilized and are used prophylactically or therapeutically to remove selected nucleic acids, including DNA and ribonucleic acid (RNA) within a biological system, including but not limited to those produced by cancer cells, microorganisms including bacteria, yeast, fungi, and viruses, and more specifically, to remove metastatic DNA and metastatic RNA in a bloodstream of the patient by passage of the blood of the patient over the bioreactor surface in a blood treatment device without adding any chemicals to the blood of the patient until the metastatic DNA and RNA have been reduced to predetermined levels.

* * * * *